United States Patent [19]

Ichikawa et al.

[11] Patent Number: 5,180,676
[45] Date of Patent: Jan. 19, 1993

[54] METHOD OF CULTIVATING ANIMAL OR PLANT CELLS

[75] Inventors: Yataro Ichikawa, Tokorozawa; Kimihiko Hamamoto, Hino; Michiyuki Tokashiki, Hachioji, all of Japan

[73] Assignee: Teijin Limited, Osaka, Japan

[21] Appl. No.: 668,473

[22] Filed: Mar. 13, 1991

Related U.S. Application Data

[63] Continuation-in-part of Ser. No. 342,685, Apr. 26, 1989, abandoned, which is a continuation of Ser. No. 744,685, Jun. 14, 1985, abandoned.

[30] Foreign Application Priority Data

Jun. 14, 1984 [JP] Japan .................. 59-120724
Jul. 27, 1984 [JP] Japan .................. 59-155424
Nov. 30, 1984 [JP] Japan .................. 59-251972

[51] Int. Cl.$^5$ .......... C12N 5/00; C12N 5/02; C12N 5/04; C12N 5/06
[52] U.S. Cl. .............. 435/240.1; 435/240.2; 435/240.21; 435/240.23; 435/240.24; 435/240.242; 435/240.3; 435/240.31; 435/240.4; 435/240.45; 435/240.54
[58] Field of Search ............ 435/240.1, 240.2, 240.21, 435/240.25, 240.26, 240.27, 270.3, 240.31, 240.4, 240.45, 240.46, 240.47, 240.54, 240.23, 240.24

[56] References Cited

U.S. PATENT DOCUMENTS 3,850,753 11/1974 Chibata et al. ............ 435/248
3,997,396 12/1976 Delente .................. 435/240.242
4,302,905 12/1981 Vasseen .................. 435/240.54

OTHER PUBLICATIONS

Matthiason, et al. (1983) "Use of perfluorochemicals for oxygen supply to immobilized cells" Annals of the New York Academy of Sciences, USA vol. 413: 545–547.
Adlerereutz, et al. (1982) "Oxygen supply to immobilized cells" European Journal of Applied Microbiology vol. 16:165–170.
Damiano et al. (1985) "Normal use of a perfluorocarbon for supplying oxygen to aerobic submerged cultures" Biotechnology Letters, vol. 7:81–86.
Glacken et al. (1983) "Mammalian cell culture: engineering principles and scale-up" Trends in Biotechnology vol. 1:102–108.

Primary Examiner—Robert A. Wax
Assistant Examiner—Gabriele E. Bugaisky
Attorney, Agent, or Firm—Wenderoth, Lind & Ponack

[57] ABSTRACT

A method of cultivating animal or plant cells, which consists essentially of contacting a cultivation liquor having animal or plant cells suspended therein with a liquid fluorocarbon having molecular oxygen dissolved therein, characterized in that said cultivation liquor forms a continuous suspension phase which has cell densities of at least $4 \times 10^6$ cells/ml, that said contact is made by feeding said liquid fluorocarbon into the cultivation liquor from above the cultivation liquor such that 1 ml of liquid fluorocarbon has a surface area of about 6 to about 300 cm$^2$ whereby the liquid fluorocarbon falls downward through the cultivation liquor by gravity, and that said cultivation liquor has a volume of at least about 10 liters.

17 Claims, 7 Drawing Sheets

FIG. 3
FIG. 4
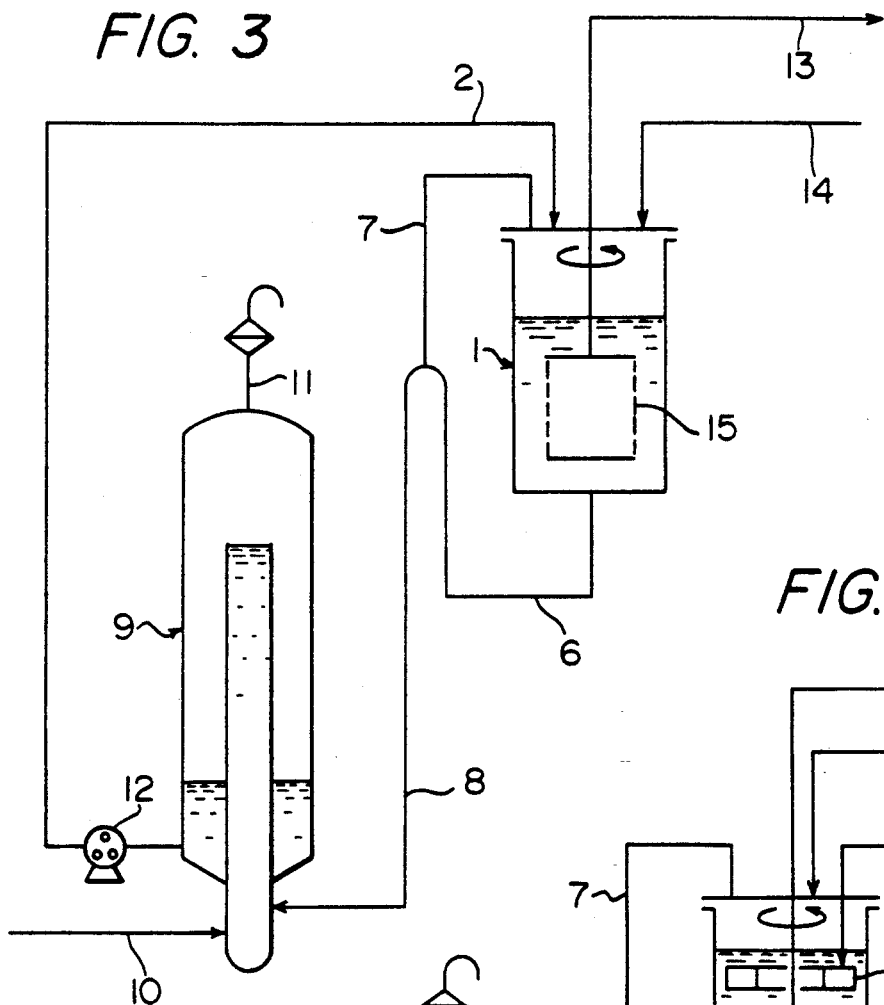
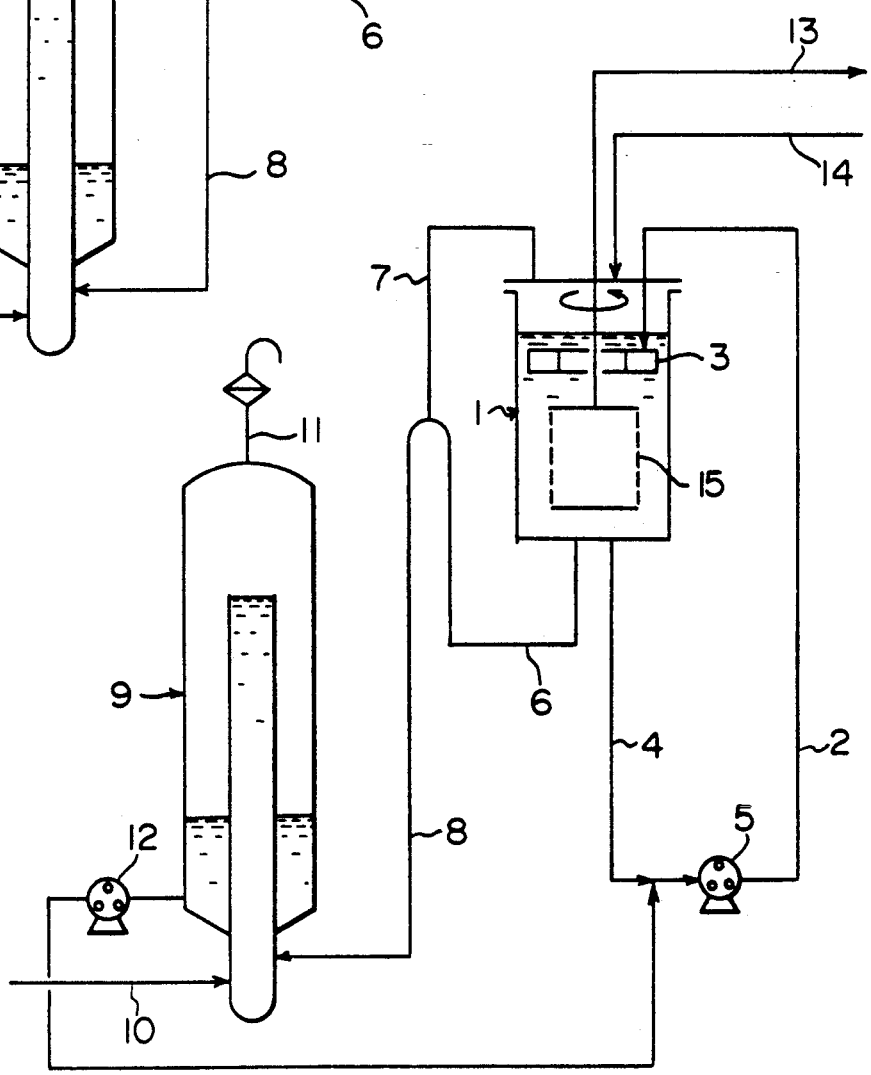

METHOD OF CULTIVATING ANIMAL OR PLANT CELLS

This application is a continuation-in-part application of Ser. No. 07/342,685 filed on Apr. 26, 1989, which is continuation application of Ser. No. 06/744,685 filed on June 14, 1985, both now abandoned.

SUMMARY OF THE INVENTION

This invention relates to a method of cultivating animal and plant cells. More specifically, it relates to a method of cultivating animal and plant cells in a industrial scale cultivation system into which oxygen is easily and efficiently supplied, whereby their growth is markedly increased.

BACKGROUND OF THE INVENTION

Cultivation of animal cells, especially in large quantities, is essential to the production of antiviral agents such as viral vaccines and interferon or biologically active chemicals such as hormones. In particular, the production of monoclonal antibodies having the ability to bind to a specified protein as a target relies on the cultivation of a large quantity of a hybridoma obtained by fusing antibody-producing cells with myeloma cells, and the solution of problems associated with this technique is an industrially important subject.

Heretofore, cell culture has been carried out on a laboratory scale by using a Petri dish, a test tube, a cultivation bottle, etc. Generally, the cell culture is classified into anchorage dependent cell culture and suspension culture depending upon the cells to be cultivated. The suspension culture would be an industrially advantageous method since it has a possibility of cultivating cells at a high density.

Cell cultures usually demand supply of oxygen ($O_2$), and for this purpose, the concentration of oxygen in the suspension is maintained constant by, for example, supplying an oxygen-containing gas from the gaseous phase above the liquid surface of the suspension and dissolving it in the suspension, or by blowing an oxygen-containing gas into the suspension. The supply of oxygen by these methods does not particularly give rise to any problem in the cultivation of cells on a small scale.

But where cell culture is desired to be effected on an industrial scale, above all at a high cell density, all of the above methods of oxygen supply are unsuitable. In the case of supplying oxygen from the free liquid surface of the suspension, even when the amount of the suspension increases, the area of the liquid surface cannot be increased correspondingly. Thus, on an industrial scale, it is almost impossible to avoid the insufficiency of oxygen supply.

When the oxygen-containing gas is blown into the suspension, the liquid surface rises owing to bubbling, and it is sometimes even difficult to continue the operation. Furthermore, this method is difficult to apply to cells which might die or decrease in proliferating activity upon contact with bubbles, or to cells which undergo a separation phenomenon by the action of bubbles (a certain kind of plant cells, for example).

Recently, a different method was proposed in Japanese Patent Publication No. 4235/1982. This patent document discloses a method of cultivating cells which comprises adhering cells to the surface of a semipermeable containing a quaternary ammonium salt having a water content of 20 to 90%, and passing a cultivation fluid over at least the opposite side to the cell-adhering surface of the membrane. This method is characterized by the fact that nutrients and oxygen are supplied to the cells through the semipermeable membrane without direct contact of the cells with the cultivation fluid.

The cultivation of plant cells has the same problem as the cultivation of animal cells. It is known that the cultivation of plant cells can give the same substances as primary or secondary metabolites obtained from the parent plants, such as enzymes, terpenoids, flavonoids, steroids, alkaloids, quinones and phenols, and useful substances in the fields of medicines, foods, cosmetics and fine chemicals. It is very important therefore to solve the same problem of the cultivation of plant cells as in the case of the cultivation of animal cells.

Science, volume 219, pages 1448–1449, March 1983 discloses a method in which a fluorocarbon emulsified and stabilized with polylysine is used as a microcarrier, and anchorage-dependent cells are cultivated on the microcarrier.

U. S. Pat. No. 3,850,753 discloses a method of cultivating an aerobic microorganism in the presence of a water-immisicible inert liquid fluorocarbon under aeration, agitation and/or shaking.

It is an object of this invention to provide a novel method of suspension cultivation on an industrial scale of animal and plant cells.

BRIEF DESCRIPTION OF THE DRAWINGS

FIG. 3—A glass device for cell culture similar to FIG. 1, with an attached bubble tower 9.

FIG. 4—A glass device for cell culture similar to FIG. 3, with the modification of a sparger 3 for dispersing fluorocarbon.

DETAILED DESCRIPTION OF THE INVENTION

Figure 1:
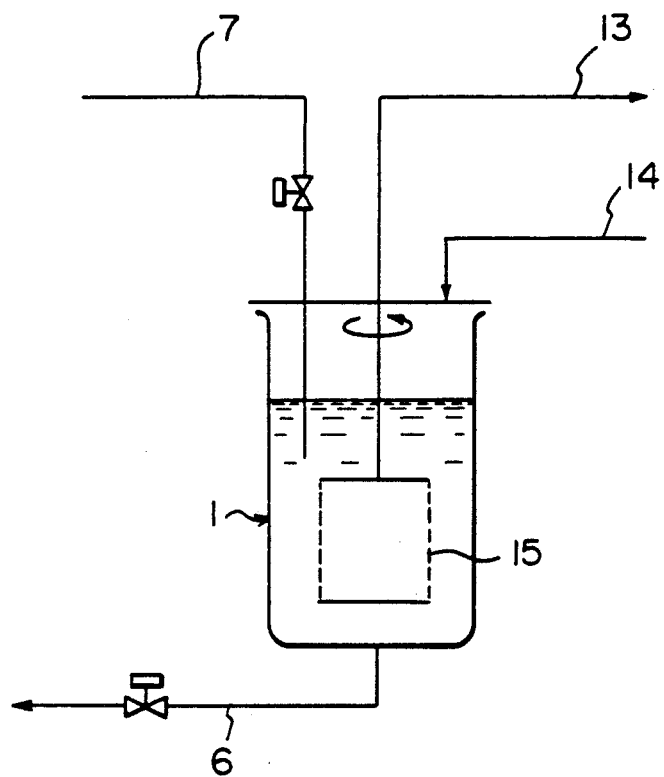
FIG. 1—A glass device for cell culture, to allow addition of air of fluorocarbon to the upper portion of the culture by line 7 and removal of fluorocarbon from the bottom by line 6.

Another object of this invention is to provide an industrially advantageous cultivation method whereby an amount of oxygen necessary and sufficient for the proliferation of animal and plant cells can be supplied to a suspension cultivation system having a industrial scale even at a considerably high cell density, for example, at least $4 \times 10^6$ cells/ml for animal cells, by the presence of a liquid fluorocarbon showing a specific range of surface area in the suspension cultivation system, and the liquid fluorocarbon which has supplied oxygen can be easily separated and recovered from the animal or plant cells.

Still another object of this invention is to provide a novel cultivation method whereby an amount of oxygen necessary and sufficient for proliferation can be supplied very smoothly and easily to animal or plant cells substantially without any deleterious effect on the cells.

Yet another object of this invention is to provide a high density and a industrial scale-cultivation method in which oxygen can be supplied smoothly throughout the cultivation system to a cultivation fluid having animal or plant cells suspended therein whereby the cell density can be increased to at least 10 times, for example, in comparison with a conventional method.

A further object of this invention is to provide an industrially advantageous cultivation method in which oxygen can be supplied to a cultivation fluid having animal or plant cells suspended therein without vigorously bubbling the cultivation fluid whereby deactivation of a useful metabolite accumulated in the cultivation fluid can be inhibited.

A still further object of this invention is to provide a method useful for industrial cultivation, in which a fluorocarbon which has supplied molecular oxygen is withdrawn from the cultivation system, and after blowing molecular oxygen into it, recycled to the cultivation system.

An additional object of this invention is to provide a method of cultivating animal or plant cells susceptible to damage by agitation or the like in which without performing an external operation of positively agitating the cultivation system, the cultivation fluid moves incident to the falling of a fluorocarbon through the cultivation system and a gentle but effective agitating action occurs in the cultivation system whereby the animal or plant cells can be cultivated without damage by the agitation.

Other objects of this invention along with its advantages will become apparent from the following description.

In accordance with this invention, the above objects and advantages of this invention are achieved by a method of cultivating animal or plant cells, which comprises contacting a cultivation liquor having animal or plant cells suspended therein with a liquid fluorocarbon having molecular oxygen dissolved therein, characterized in that said cultivation liquor forms a continuous suspension phase which has cell densities of at least $4 \times 10^6$ cells/ml, that said contact is made by feeding said liquid fluorocarbon into the cultivation liquor from above the cultivation liquor such that 1 ml of liquid fluorocarbon has a surface area of about 6 to about 300 $cm^2$ whereby the liquid fluorocarbon falls downward through the cultivation liquor by gravity, and that said cultivation liquor has a volume of at least about 10 liters, preferably at least about 30 liters.

According to the method of this invention, the cultivation liquor having animal or plant cells suspended therein and the liquid fluorocarbon having molecular oxygen dissolved therein are directly contacted with each other whereby through the contacting surfaces of the two phases, oxygen from the liquid fluorocarbon phase dissolves in the cultivation liquor and an amount of oxygen necessary and sufficient for cultivation of the animal cells can be supplied.

Investigations of the present inventors have shown that even when the aforesaid direct contact of the liquid fluorocarbon with the cultivation liquor results in direct contact between the cells and the fluorocarbon, the cells are stable both chemically and physically and proliferate without any adverse effects on their growth, and that cultivation of the cells at a high density and at industrial scale which requires a large amount of oxygen can be achieved without any troubles even when the fluorocarbon is supplied in a large quantity.

In the method of this invention, the cultivation liquor form a continuous phase. The liquid fluorocarbon should be present in the other continuous phase such that 1 ml of liquid fluorocarbon shows a surface area of about 6 to about 300 $cm^2$. The surface area shown by 1 ml of the liquid fluorocarbon is preferably about 10 to about 200 $cm^2$, more preferably 15 to 150 $cm^2$. The surface area of the liquid fluorocarbon does not include that of an interface between the continuous phase and a precipitated phase formed after it has gone past the continuous phase.

The liquid fluorocarbon used in the method of this invention has an excellent ability to dissolve molecular oxygen in regard to the amount and the speed in and at which it dissolves molecular oxygen. The liquid fluorocarbon is not miscible with the cultivation liquor, and is substantially nontoxic to animal or plant cells. Preferably, the liquid fluorocarbon used in the method of this invention is a liquid perfluorocarbon. Examples of the liquid fluorocarbon include perfluoroalkanes having 6 to 20 carbon atoms, perfluorocycloalklanes having 5 to 14 carbon atoms which may be substituted by perflluoroalkyl groups having 1 to 5 carbon atoms, perfluorotetrahydrofurans substituted by perfluoroalkyl groups having 1 to 5 carbon atoms, perfluorotetrahydropyrans substituted by perfluoroalkyl groups having 1 to 5 carbon atoms, perfluoroadamantanes which may be substituted by perfluoroalkyl groups having 1 to 5 carbon atoms, and tertiary amino group-substituted products of the above fluorocarbons.

Specific examples of the perfluoroalkanes having 6 to 20 carbon atoms are linear or branched perfluoro-n-heptane, perfluorooctane and perfluorononane.

Specific examples of the perfluorocycloalkanes having 5 to 14 carbon atoms which may be substituted by perfluoroalkyl groups having 1 to 5 carbon atoms are perfluoro-1-trimethyldecalin and perfluorodecalin.

Specific examples of the perfluorofurans or perfluorotetrahydrofurans substituted by perfluoroalkyl groups having 1 to 7 carbon atoms are perfluoro-2-butylperfluorofuran, perfluoro-2-butyltetrahydrofuran, perfluoropentyl perfluorofuran, perfluoropentyl tetrahydrofuran, perfluorohexyl perfluorofuran, perfluorohexyl tetrahydrofuran, perfluoroheptyl perfluorofuran, and perfluoroheptyl tetrahydrofuran.

Specific examples of the perfluorfurans or tetrahydropyrans substituted by perfluoroalkyl groups having 1 to 6 carbon atoms include perfluorobutyl perfluoropyran, perfluorobutyl tetrahydropyran, perfluoropentyl perfluoropyran, perfluoropentyl tetrahydropyran, perfluorohexyl perfluoropyran, and perfluorohexyl tetrahydropyran.

Specific examples of the perfluoroadamantanes which may be substituted by perfluoroalkyl groups having 1 to 5 carbon atoms are perfluoroadamantane, perfluoromethylperfluoroadamantane, perfluorodimethylperfluoroadamantane, perfluoromethylperfluoroethylperfluoroadamantane and perfluorodimethylperfluoroadamantane.

Examples of the tertiary amino group substituted products of these fluorocarbons are perfluorotributylamine-substituted products and perfluoro-N-methylmorpholine substituted products of these fluorocarbon.

These liquid fluorocarbons may be used singly or in combination.

As stated hereinabove, the method of this invention is carried out while one of the cultivation liquor is used as a continuous phase and the liquid fluorocarbon, as a separated phase. In this invention, the separated phase (liquid fluorocarbon) may be in the form of, for example, a liquid droplet, a liquid column, or a liquid film. It is preferred that 1 ml of liquid fluorocarbon forms a liquid droplet showing a surface area of about 6 to about 300 $cm^2$, especially 10 to 200 $cm^2$.

Generally, the liquid fluorocarbon shows a specific gravity about 1.6 to about 2 times that of water. Accordingly, in the practice of the method of this invention, it is advantageous to utilize this high specific gravity of the liquid fluorocarbon.

According to this invention, the liquid fluorocarbon having molecular oxygen dissolved therein may be fed into the continuous phase from above the continuous phase whereby the liquid fluorocarbon, in the form of, for example, a liquid droplet, column or film, falls by gravity through the continuous phase (cultivation liquor).

In this invention the liquid fluorocarbon which has fallen by gravity through the cultivation liquor supplies molecular oxygen to the cultivation liquor and forms a precipitated phase upon arrival at the bottom of the cultivation tank. The precipitated phase can be separated from the cultivation liquor by a suitable operation.

In the embodiments of this invention, as the liquid fluorocarbon moves downwardly from the above the cultivation liquor as a liquid drop, column or film, an agitation action occurs throughout the cultivation liquor. This agitating action is gentle but very efficient, and for this reason, molecular oxygen can be smoothly supplied from the liquid fluorocarbon to the cultivation liquor without applying a positive agitating operation externally to the cultivation system.

The precipitated phase can be recycled to the cultivation system. For example, the cultivation method involving recycling of the precipitated phase can be advantageously carried out by a combination of the following four steps.

(1) Feeding a liquid fluorocarbon having molecular oxygen dissolved therein from above into a cultivation tank containing a continuous phase of a cultivation liquor having animal or plant cells suspended therein in a density of at least $4 \times 10^6$ cells/ml to thereby contact them with each other while 1 ml of the liquid fluorocarbon has a surface area of about 6 to about 300 $cm^2$, said cultivation liquor having a volume of at least about 10 liters, preferably about 30 liters;

(2) withdrawing a heavy phase (precipitated phase) composed substantially of the fluorocarbon from the bottom of the cultivation tank;

(3) dissolving molecular oxygen in the fluorocarbon in the heavy phase, and (4) thereafter using the liquid fluorocarbon having molecular oxygen dissolved therein in step (1).

Furthermore, the method of this invention, can be conveniently carried out by a perfusion method which comprises separating and withdrawing the cultivation liquor from the cultivation system composed substantially of the liquid fluorocarbon, the cultivation liquor and the animal or plant cells, continuously or stepwise, and supplying a fresh liquid medium in an amount corresponding to the withdrawn cultivation liquor to the cultivation system continuously or stepwise.

The fresh liquid medium contains nutrients, salts, etc. required for cultivation. When animal cells are to be cultivated, the fresh liquid medium is formed by adding components normally used in cell cultures, such as various inorganic salts, vitamins, coenzymes, glucose, amino acids and antibiotics to an aqueous medium composed substantially of water. Serum may be added to the culture medium. It is also possible to use a so-called serum-free medium for cultivation. When plant cells are to be cultivated, the fresh liquid medium is formed by adding components normally used in plant cell cultures, such as various inorganic salts, vitamins, inositol, sucrose, and plant hormones (such as auxin and cytokinin). It is also possible to add amino acids, coconut milk, casein hydrolyzate, yeast extracts and glucose to the cultivation liquor. Usually, the cultivation liquor is used in a pH range of 4.0 to 6.5.

The cultivation liquor may be separated from the cultivation system by, for example, using a microfilter, a semipermeable membrane, etc. Since the culti vation liquor withdrawn from the cultivation system contains wastes and metabolites of the cells, etc. and other growth inhibiting substances, its withdrawing from the cultivation tank is desirable for efficient proliferation of cells. It is particularly advantageous to grow the cells at a high density.

The cultivation method of this invention can be applied both to animal and plant cells.

Examples of the animal cells to which the method of this invention can be applied include cells capable of producing useful substances, such as BALL-1 cells, TALL-1 cells, NALL-1 cells (I. Miyoshi, Nature, 267, 843, 1977), Namalwa cells (Journal of Clinical Microbiology, 1, 116, 1975), M-7002 cells, B-7101 cells (Journal of Immunology, 113, 1334, 1974), Flow 7000 cells (Flow Company, U.S.A.), JBL cells, EBV-SA cells, EBV-WA cells, and FBV-HO cells ("Tissue Culture", 6, 527, 1980) which are lymphotoxin-producing cells; JAX cells such as Jurket cells or Jurket-FHCRC cells, JP111 (ATCC CRL 8120) which are interleukin 2-producing cells; Namalwa cells which are IFN-producing cells; and hybridomas, transformed cells, cancer cells, and genetically manipulated cells.

Examples of the hybridomas are mouse-mouse hybridoma, mouse-human hybridoma, human-human hybridoma and (mouse-human)-human hybridoma. Parent strains of these hybridomas, are for example, P3-NS1-1-AG4-1, P3-X63-Ag8, P3-X63-Ag8-U1, MPC11-45.6.TG1.7, SP2/0-Ag14X63-Ag8-6.5.3, 210RCY.Ag1.2.3, SKO-007GM15006 TG-A12, and cells transfected with viruses. Examples of cells to be fused with these parent strains are B cells, T cells and macrophage.

Examples of the transformed cells are cells transformed with EB virus and SV40 transformed human fetal lungs.

Examples of the cancer cells are myeloma, hepatoma, carcinosarcoma, osteosarcoma, melanoma, colon adenocarcinoma and medulloblastoma.

The genetically manipulated cells include, for example, those in which the host cells are mouse L cells, NIH/3T3, CHO (ovary cells of Chinese hamster), ovary cells of armyworms, mouse myeloma, and C127 (epithelial) cells derived from mouse breast cancer).

Those anchorage-independent animal cells can be directly suspended in the liquid cultivation medium without carrying them on a carrier. Or they may be immobilized with a gel before suspending them in the liquid cultivation medium. On the other hand, anchorage-dependent animal cells can be suspended in the cultivation liquor while carrying them on a carrier. Such anchorage-dependent cells are, for example, vero cells, and human diploid foreskin fibroblasts.

According to the method of this invention, animal cell densities of at least $4 \times 10^6$ cells/ml, preferably at least $6 \times 10^6$ cells/ml, in the cultivation liquor may be preferably employed in the cultivation of these animal cells.

The plant cells to which the method of this invention can be applied include, for example, those derived from higher plants or phanerogamous plants. These cells include those modified artificially or by gene manipulation. Modification may be performed between cells of the same kind having different cell properties with respect to, for example, the content of a useful substance and the speed of cell proliferation, or between cells of taxonomically different plants in terms of species, genus and family.

Specific examples include cells of *Nicotiana tabacum, Nicotiana rustica, Atropa belladonna, Datura stramonium, Datura innoxia, Datura meteloides, Datura tatula, Datura metel, -Hyoscyamus niger, Duboisia myoporoides, Scopolia, japonica, Scopolia poruiflora, Peganum harmala, Conium maculatusm, Catharanthus roseus, Rauwolfia serpentian, Digitalis purpurea, Digitalis lanata, Papauer somniferum, Papaver bracteatum, Vincaminr, Coptis japonica, Phellodendron amurense, Phaseolus vulgaris, Camptotheca acuminate, Cephalotaxus harringtonia, Triptergium wilfordii, Ruta graveolens, Phytolacca americana, Agrostemma githago, Beta vulgaris, Cucurma longa, Chenopodium centrorubrum, Derris elliptica, Chrysanthmum cinedrariaefolium, Stephania cepharantha, Isodun japonicus, Dioscorea deltoidea, Crocus sativus, Dioscorea japonica, Dioscorea emposita, Dioscorea tokoro, Sophora angustifolia, Stevia rebaudiana, Yuicca glauca, Achyranthes japonica, Panax ginseng, Lithospermum erythrorhizon, Rheum palmatus, Carthamus tinctorius, Bupleurum faleatum, Cassia angustifolia, Salvia miltiovhiza, Cassia obutsifolia, Morinde citrifolia, Mucuna pruriens, Erythroxylon coca, Colchicum autumnale, Ailanthus altissima, Brucea antidysenterica, Maytenus buchanani, Epimedium grandiflorum, Putterlickia vercosa, Cephaelis ipecacuanba, Glycyrrhiza glabra, Gynostemma pentaphyllum, Heliotropium indicum, Podophyllum emodi, Jaxus brevifolia, Rose damascona, Rose centifolia, Jasminum officinale, Jasminum grandiflorum, Matricaria chamomilla, Lavendula officinalis, Angelica archangelica, Salvia offcinalis, Mentha arvensis, Mentha piperita, Mentha viridis, Pelargonium denticulatum, Hydrangea serrata, Cochlearia oblongifolio, Capsicum annuum, Achras sapota, Wasabia japonica, Euphorbia tirucalli, Oryza sativa, Triticum vulgare, Hordeum vulgare, Hordeum clistichum, Zea mays, Sorghum nervosum, Glycine max, Phaseolus vulgaris, Pisum sativum, Ipomoea batatas, Dioscorea batatas, Allium cepa, Allium fislulosum, Allium satwum, Solanum tuberosum, Manihot utilissima, Raphanus sativus, Daucus carota, Coloacsia plantaginea, Brassica napus, Hellianthus annuus, Spinacia oleracea, Asparagus officinalis, Brassica oleracea, Brassica pekinensis, Apium graveolens, Retroselinum sativum, Lactuca sativa, Brassica rapa, Fragaria chiloensis, Vicia faba, Hycoipersicum esculentum, Solanum melonyena, Citrullus vulgaris, Cucumis sativus, Cucumis melo, Ananas comosus, Cucurbita maxima, Cucurbita pepo, Trifolium pratense, Trifolium repens, Medicago sativa, Dactylis glomerata, Phleum pratens, Musa sapientum, Cocos nucifera, Diospyros kaki, Prunus persica, Malus pumila, Prunus avium, Prunus carasus, Pyrus serotina, Pyrus communis, Prunus communis, Vitis vinifera, Citrus lemon, Citrus unshiu, Citrus sinensis, Olea europaea, Vaccinium pennsylvanicum, Vaccinium canadense, Gossypium hirsutum, Gossypium barbadense, Sossypiuum arboreum, Cammellia sinensis, Cofea arabica, Humulus lupulus, Saccharum officinarum, Elaeis guineensis, Chrysanthemum morifolium, Dianthus caryophyllus, Rosa chinensis, Lillium longiflorum, Lililum aurantum, Tulipa generiana, Gerbera jamesonii and Narcissus tazetta.*

These cells may be fused cells obtained between cells or cultivated cells, or between cultivated cells and cells directly obtained from plant tissues, or between cells obtained directly from plant tissues.

The following examples illustrate the present invention more specifically.

In these examples, the surface area of a liquid fluorocarbon in the cultivation system was measured by the following method.

The size of the separated phase is examined from the side of the cultivation tank (preferably when the separated phase begins to form), and the surface area is calculated from the examined size.

When the separated layer is in the form of liquid droplets, the cultivation system is photographed from the side of the cultivation tank. The sizes of all of the liquid droplets (separated phase) having a clear contour in the photograph are calculated, and the average surface area of the separated phase is calculated from the calculated sizes.

When the separated phase is in the form of a liquid column or film, the cultivation system is photographed from the side of the cultivation tank at various angles so that its sectional area taken in a direction perpendicular to the vertical direction can be calculated as accurately as possible. The sectional areas are calculated from the resulting photographs, and the average surface area of the separated phase is calculated from the calculated values.

EXAMPLE 1

A device shown in FIG. 1 of the accompanying drawings was used. A glass fermentor 1 (having a diameter of 80 mm and a height of 140 mm) including a cylindrical rotating filter having a height of 35 mm and an outside diameter of 60 mm (impermeable to cells but permeable to liquid components; G-5 glass fiber in the present example) was sterilized in an autoclave. The fermentor was then charged with 225 ml of RPMI 1640 medium containing 10% fetal bovine serum, and mouse-mouse hybridoma 4C10B6 cells (parent strain: P3U1) were seeded at a density of $1.5 \times 10^5$ cells/ml (these cells produce IgG2b antibody). Air containing 5% $CO_2$ was passed through the top portion of the fermentor, and the cells were cultivated at 37° C. while rotating the rotating filter at 150 rpm.

On the third day, the cell density was measured. Living cells were found to exist at a density of $9.2 \times 10^5$ cells/ml, and no dead cells were observed. The antibody concentration was 45 micrograms/ml.

On the third day and thereafter, a fresh medium of the above composition was continuously fed at a rate of 450 ml/day from line 14 in FIG. 1. Simultaneously, the cultivation liquor was continuously separated from the cells and taken out of the system through line 13 via filter 15 by means of a pump fitted to the end of the line 13 so that the volume of cultivation liquor in the fermentor became constant at 225 ml. On the 4th day, the concentration of dissolved oxygen in the fermentor dropped below 3 ppm. Therefore, the supplying of air containing 5% $CO_2$ was stopped, and from line 7, Fluorinert FC-40 (a trade name for a fluorocarbon produced by 3M Company) having oxygen dissolved therein was added dropwise from the top of the fermentor so that the amount of dissolved oxygen in it became 3 ppm. The average surface area of the fluorocarbon at this time was 11 $cm^2$/ml.

The fluorocarbon settled to the bottom of the fermentor, but was taken out of the system through line 6 so that the interface between it and the cultivation liquor was maintained at a constant level. On the 6th day and thereafter, the rate of feeding the fresh medium from line 14 was changed to 6-75 ml/day.

The operability of the above high-density continuous cultivation by the perfusion method was good. The cell densities and the antibody concentrations in the cultivation liquor were as follows.

TABLE 1

| Time | Cell density (cells/ml) | | Concentration of the antibody (micrograms/ml) |
|---|---|---|---|
| | Living cells | Dead cells | |
| 1st day | $1.5 \times 10^5$ | 0 | — |
| 3rd day | $9.2 \times 10^5$ | 0 | 45 |
| 4th day | $2.0 \times 10^5$ | 0 | — |
| 5th day | $4.0 \times 10^6$ | $2.4 \times 10^5$ | 68 |
| 6th day | $6.2 \times 10^6$ | $3.4 \times 10^5$ | 97 |
| 7th day | $8.3 \times 10^6$ | $2.7 \times 10^5$ | 97 |
| 8th day | $1.1 \times 10^7$ | $2.9 \times 10^5$ | 130 |

COMPARATIVE EXAMPLE 1

Figure 2:
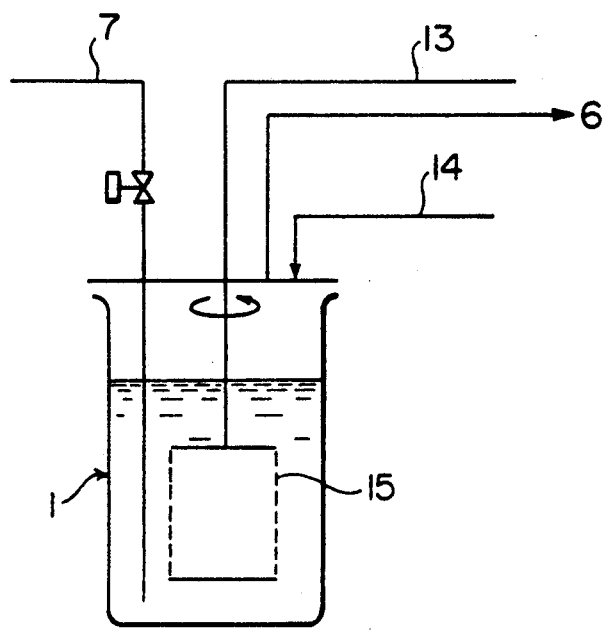
FIG. 2—A glass device for cell culture, with line 7 to deliver gas to the medium and allow formation of a bubble layer at the top.

A device shown in FIG. 2 was used. A gas blowing tube (a glass tube fitted at its tip with a G-3 glass filter) was fitted to a fermentor of the same size as used in Example 1, and the device was sterilized in an autoclave. Thereafter, 225 ml of RPMI 1640 medium containing 10% fetal bovine serum was charged into the fermentor, and mouse-mouse hybridoma 4C10B6 strain (parent strain: P3U1) was seeded in the medium at a cell density of $1.5 \times 10^5$ cells/ml This cell was capable of producing $IgG_{2b}$ antibody. Air containing 5% of $CO_2$ was passed through the upper portion of the fermentor, and the cultivation was carried out at 37° C. while the rotating filter was rotated at 150 rpm. The cell density measured on the third day was $1.1 \times 10^6$ cells/ml, and no dead cell was observed. The concentration of the antibody produced was 48 micrograms/ml.

On the third day, continuous feeding of a fresh medium of the above composition from line 14 in FIG. 2 was started at a rate of 450 ml/day. At the same time, the cultivation liquor was continuously separated from the cells and taken out of the system through line 13 via a filter 15 by means of a pump fitted to the end of line 13 so that the volume of the cultivation liquor in the fermentor was maintained constant at 225 ml. On the 4th day, the concentration of dissolved oxygen in the fermentor fell below 3 ppm. Therefore, air containing 5% $CO_2$ was blown into the fermentor from gas-blowing line 7 so that the concentration of dissolved oxygen became 3 ppm. As soon as the air blowing was started, a bubble layer having a thickness of about 10 mm was formed in the upper portion of the cultivation liquor. The cell densities were measured, The density of living cells was $1.7 \times 10^6$ cells/ml, and the density of dead cells was $3.0 \times 10^5$ cells/ml. On the fifth day, the height of the bubble layer became about 30 mm. The density of living cells was $3.8 \times 10^6$ cells/ml, and the density of dead cells was $1.2 \times 10^6$ cells/ml. The concentration of the antibody was 58 micrograms/ml. On the 6th day, the bubble layer became high, and flowed out into gas discharging line 6 to make the continuous operation impossible. Therefore, the experiment was stopped. At this time, the density of living cells was $5.1 \times 10^6$ cells/ml, and the density of dead cells was $2.1 \times 10^6$ cells/ml. The concentration of the antibody was 80 micrograms/ml.

EXAMPLE 2

A device shown in FIG. 3 of the accompanying drawings was used. A glass fermentor 1 having a diameter of 80 mm and a height of 140 mm including a cylindrical rotating filter having a height of 35 mm and an outside diameter of 60 mm (impermeable to cells but permeable to liquid components; G-5 glass fiber in the present example) was sterilized in an autoclave. The fermentor was then charged with 225 ml of RPMI 1640 medium containing 10% fetal bovine serum, and mouse-mouse hybridoma C10B6 cells (parent strain: P3U1) were seeded at a density of $1.5 \times 10^5$ cells/ml (these cells produce IgG2b antibody). Air containing 5% $CO_2$ was passed through the upper portion of the fermentor, and the cells were cultivated at 37° C. while rotating the rotating filter at 150 rpm.

On the third day, the cell density was measured Living cells were found to exist at a density of $9.0 \times 10^5$ cells/ml, and no dead cells were observed.

On the third day, continuous feeding of a fresh medium of the above composition was started at a rate of 450 ml/day from line 14 in FIG. 3. Simultaneously, the cultivation liquor was continuously separated from the cells and taken out of the system through line 13 via filter 15 by means of a pump fitted to the end of the line 13 so that the volume of cultivation liquor in the fermentor became constant at 225 ml. On the 4th day, the concentration of dissolved oxygen in the fermentor dropped below 3 ppm. Therefore, the supplying of air containing 5% $CO_2$ was stopped, and from line 2, Fluorinert FC-40 (a product of 3M Company) having oxygen dissolved so that the amount of dissolved oxygen in it became 3 ppm. The average surface area of the fluorocarbon at this time was 21 $cm^2$/ml.

A fluorocarbon-withdrawing line 6 is attached to the bottom of the fermentor 1, and a communication line 7 leading to the fermentor is connected to this line so that the position of the interface between the fluorocarbon and the cultivation liquor can be controlled automatically at a fixed position. The position of the interface between the cultivation liquor and the fluorocarbon in the fermentor 1 can be set at a desired level by changing the position of the connecting part between the lines 6 and 7. The fluorocarbon introduced into the cultivation system was automatically supplied to a bubble tower 9 through lines 6 and 8 while its amount residing in the system was maintained constant. Oxygen gas containing 5% $CO_2$ sterilized through a filter was continuously blown into the bubble tower 9 from its bottom portion through line 10. The fluorocarbon which had oxygen fully dissolved in it in the inside member of the bubble tower 9 resided at the bottom portion of the outside member of the tower. The fluorocarbon was supplied to the cultivation system through line 2 by means of a pump 12 so that the concentration of dissolved oxygen in the cultivation system became 3 ppm.

On the sixth day and thereafter, the rate of feeding the fresh medium from line 14 was changed to 675 ml/day.

The cell densities and the antibody concentrations were measured, and the results are shown in Table 2.

TABLE 2

| Time | Cell density (cells/ml) | | Concentration of the antibody (micrograms/ml) |
|---|---|---|---|
| | Living cells | Dead cells | |
| 1st day | $1.5 \times 10^5$ | 0 | 0 |
| 3rd day | $9.0 \times 10^5$ | 0 | 32 |
| 4th day | $1.9 \times 10^6$ | 0 | 28 |
| 6th day | $6.5 \times 10^6$ | $2.3 \times 10^5$ | 64 |
| 8th day | $1.2 \times 10^7$ | $2.1 \times 10^5$ | 138 |
| 9th day | $1.4 \times 10^7$ | $3.2 \times 10^5$ | 173 |

EXAMPLE 3

Thirty milliliters of the modified Murashige Skoog medium described in Table 3 below and 30 ml of Fluorinert FC-40 (a fluorocarbon made by Sumitomo 3M Company) were introduced into a 100 ml Erlenmeyer flask equipped with a dropping port for adding the fluorocarbon dropwise at the upper portion of the flask and a discharge opening for discharging the fluorocarbon at its lower portion and adapted to circulate the fluorocarbon externally. Cultivated cells (green-colored) of *Nicotiana tabacum* Samson were seeded in an amount of 1.0 g as fresh weight. The air in the upper portion of the flask was replaced by nitrogen, and the flask was stopped. Fluorinert FC-40 having dissolved oxygen in it by aseptic aeration was circulated by means of a peristatic pump by harmonizing introduction into the fermentor with discharging from it. At this time, the introduction of the fluorocarbon was effected by dropping droplets of the fluorocarbon from the dropping port at the upper portion of the flask, and the liquid was discharged from the discharge portion located in the fluorocarbon layer. At the time of dropwise addition, the average surface area of the fluorocarbon was 20 cm²/ml.

The fermentor was rotated by a rotary shaker at a speed of 120 rpm, and the cultivation was cultivated for 10 days at 25° C. under the illumination of a fluorescence lamp at about 3000 luxes.

All of the cultivated cells were harvested from the fermentor. 9.3 g, as the fresh weight, of green cells were obtained. This shows that the cells had ordinary proliferating ability.

TABLE 3

| Composition of the modified Murashige Skoog medium | |
|---|---|
| Component | Concentration (mg/liter) |
| Potassium nitrate | 1900 |
| Ammonium nitrate | 1650 |
| Calcium chloride dihydrate | 440 |
| Magnesium sulfate heptahydrate | 370 |
| Potassium dihydrogen phosphate | 170 |
| [Trace Components] | |
| Boric acid | 6.2 |
| Manganese sulfate tetrahydrate | 22.3 |

TABLE 3-continued

| Composition of the modified Murashige Skoog medium | |
|---|---|
| Component | Concentration (mg/liter) |
| Zinc sulfate tetrahydrate | 8.6 |
| Potassium iodide | 0.83 |
| Sodium molybdate dihydrate | 0.25 |
| Copper sulfate pentahydrate | 0.025 |
| Cobalt chloride hexahydrate | 0.025 |
| [Iron Source] | |
| Iron (II) sodium ethylenediamine-tetraacetate | 38.5 |
| [Vitamins] | |
| Thiamine hydrochloride | 0.40 |
| Inositol | 100 |
| Pyridoxine hydrochloride | 0.5 |
| Nicotinic acid | 0.5 |
| Glysine | 2 |
| [Hormones] | |
| 1-Naphthaleneacetic acid | 1.86 |
| 6-Benzyladenine | 0.225 |
| [Carbon source] | |
| Sucrose | 30,000 |
| pH | 5.6 |

EXAMPLE 4

Cultivated cells (green) of *Catharanthus roseus* were cultivated for 10 days under the same conditions as in Example 3 except that in the culture medium 2,4-dichloroacetic acid was used as the hormone in a concentration of 0.1 mg/liter.

The grown cells were harvested from the fermentor. Green cells were obtained in an amount of 11.3 g as fresh weight.

The cells were lyophilized and alkaloids were extracted from the cells in a customary manner, and the residue was analyzed by high-performance liquid chromatography. Both qualitatively and quantitatively, hardly any effect by the use of Fluorinert FC-40 was observed.

EXAMPLE 5

Cultivated cells (white) of soybean (*Glycine max*) cultivated for 10 days using Fluorinert FC-75 (a fluorocarbon manufactured by Sumitomo 3M Company) (average surface area 23 cm²/ml) under the same conditions as in Example 9 except that the cultivation was carried out in the dark.

The grown cells were harvested from the fermentor, and 10.5 g, as fresh weight, of white cells were obtained. They showed the same proliferating ability as in an ordinary cultivation.

EXAMPLE 6

In the same way as in Example 3, shoots of *Digitalis purpurea* were cultivated for 21 days using perfluorodecalin (average surface area 22 cm²/ml). As a result of the cultivation, 5.3 g, as fresh weight, of shoots were harvested. They showed the same degree of proliferating ability as an ordinary cultivation.

A device shown in FIG. 4 was used. The same fermentor 1 as used in Example 1 was used. A fluorocarbon dispersing sparger 3 (made of SUS 316 stainless steel) in the fermentor 1 had four holes with a diameter of 2 mm. Each hole was bored so that its distance from central axis of a rotating filter equalled the ariththemetic average of the inside diameter of the fermentor and the outside diameter of the rotating filter 15.

The fermentor was entirely sterilized in an autoclave. The same culture medium as used in Example 1 which had been sterilized by filtration was charged into the fermentor so that the volume of the cultivation liquor became about 225 ml, and mouse-mouse hybridoma 4C10B6 was seeded at a cell density of $1.5 \times 10^5$ cells/ml. A fluorocarbon (Fluorinert FC-70) sterilized by filtration was charged into the cultivation system in the same manner as in Example 2. The rotating filter was rotated at 30 rpm. By operating pumps 5 and 12, the fluorocarbon was fed into the cultivation system, and a gas composed of 5% of $CO_2$ and 95% of $O_2$ was continuously blown into bubble tower 9 through line 10. The fluorocarbon which left the sparger 3 formed a liquid column and had an average surface area of 31 cm2/ml. The cultivation system was maintained at 37° C., and the cultivation was carried out by automatically operating and stopping the pump 12 so that the concentration of dissolved oxygen in the fermentor was 3 ppm.

On the third day, the density of living cells was $8.1 \times 10^5$ cells/ml, and no dead cells were observed.

On the third day and thereafter, the same culture medium as in Example 1 was continuously fed at a rate of 450 ml/day from line 14. At the same time, the cultivation liquor was continuously separated from the cells, and taken out of the cultivation system through the rotating filter 15 and line 13 by means of a pump fitted to the end of line 13 so that the volume of the cultivation liquor in the fermentor was maintained constant at 225 ml. On the 6th day and thereafter, the rate of feeding the fresh medium fed from line 14 was changed to 675 ml/day.

The operability of the high-density continuous cultivation by the perfusion method described above was good. The cell densities and the antibody concentrations in the cultivation liquor were measured, and the results are shown in Table 4.

TABLE 4

| Time | Cell density (cells/ml) | | Concentration of the antibody (micrograms/ml) |
|---|---|---|---|
| | Living cells | Dead cells | |
| 1st day | $1.5 \times 10^5$ | 0 | 0 |
| 3rd day | $8.1 \times 10^5$ | 0 | 29 |
| 4th day | $1.8 \times 10^6$ | 0 | 24 |
| 6th day | $6.3 \times 10^6$ | 0 | 62 |
| 8th day | $1.3 \times 10^7$ | $1.6 \times 10^5$ | 141 |
| 9th day | $1.5 \times 10^7$ | $1.4 \times 10^5$ | 163 |

EXAMPLE 8

The same cultivation as in Example 7 was carried out except that a sparger 3 having a slit, 1.5 mm wide and 2 cm long, provided at the same position as the nozzle used in Example 7 was used. By using this sparger, a fluorocarbon (Fluorinert FC-70) was formed into a liquid film having a surface area of 19 cm2/ml.

The operability of the high-density continuous cultivation by the perfusion method described above was good. The cell densities and the antibody concentrations in the cultivation liquor were measured, and the results are shown in Table 5 below.

TABLE 5

| Time | Cell density (cells/ml) | | Concentration of the antibody (micrograms/ml) |
|---|---|---|---|
| | Living cells | Dead cells | |
| 1st day | $1.5 \times 10^5$ | 0 | 0 |
| 3rd day | $9.3 \times 10^5$ | 0 | 31 |

TABLE 5-continued

| Time | Cell density (cells/ml) | | Concentration of the antibody (micrograms/ml) |
|---|---|---|---|
| | Living cells | Dead cells | |
| 4th day | $2.1 \times 10^6$ | 0 | 28 |
| 6th day | $6.7 \times 10^6$ | $1.0 \times 10^5$ | 59 |
| 8th day | $1.4 \times 10^7$ | $1.6 \times 10^5$ | 152 |
| 9th day | $1.4 \times 10^7$ | $2.1 \times 10^5$ | 171 |

EXAMPLE 9

The same cultivation as in Example 7 was carried out except that Fluorinert FC-77 was used as the fluorocarbon, and the hole diameter of the sparger 3 was changed to 0.1 mm. The average surface area of the fluorocarbon was 270 cm2/ml.

A very small portion of the cultivation liquor was entrained in the fluorocarbon, but the operability was good.

The cell densities and the antibody concentrations in the cultivation liquor were measured, and the results are shown in Table 6.

TABLE 6

| Time | Cell density (cells/ml) | | Concentration of the antibody (micrograms/ml) |
|---|---|---|---|
| | Living cells | Dead cells | |
| 1st day | $1.5 \times 10^5$ | 0 | 0 |
| 3rd day | $6.1 \times 10^5$ | 0 | 24 |
| 4th day | $1.5 \times 10^6$ | $1.2 \times 10^5$ | 19 |
| 6th day | $5.2 \times 10^6$ | $3.6 \times 10^5$ | 41 |
| 8th day | $9.0 \times 10^6$ | $8.9 \times 10^5$ | 98 |
| 9th day | $1.1 \times 10^7$ | $1.3 \times 10^6$ | 124 |

EXAMPLE 10

The cultivation of mouse-mouse hybridoma 4C10B6 cells was carried out by using the same device and method as those in Example 1 except that substances shown in Tables 7–9 below were used as oxygen supply media instead of Fluorinert FC-40. The results obtained are shown in Tables 7 to 9. Further, FC-70 and FC-72 used in Tables 8 and 9 are both trade names for fluorocarbons produced by 3M Company.

TABLE 7

Perfluoro-decalin was used as the oxygen supply medium. The average surface area of fluorocarbon was 14 cm2/ml.

| Time | Feed rate of the fresh medium (ml/day) | Cell density (cells/ml) | | concentration of the antibody (micrograms/ml) |
|---|---|---|---|---|
| | | Living cells | Dead cells | |
| 1st day | 0 | $2.3 \times 10^5$ | $1.4 \times 10^4$ | — |
| 3rd day | 0 | $7.8 \times 10^5$ | $2.1 \times 10^4$ | — |
| 4th day | 450 | $1.5 \times 10^6$ | $3.1 \times 10^4$ | — |
| 5th day | 450 | $3.1 \times 10^6$ | $7.2 \times 10^4$ | 43 |
| 6th day | 675 | $6.3 \times 10^6$ | $8.1 \times 10^4$ | 78 |
| 7th day | 675 | $1.2 \times 10^7$ | $2.1 \times 10^5$ | 106 |
| 8th day | 675 | $1.1 \times 10^7$ | $2.6 \times 10^5$ | 129 |

TABLE 8

Fluorinert FC-70 was used as the oxygen supply medium. The average surface area of FC-70 was 13 cm$^2$/ml.

| Time | Feed rate of the fresh medium (ml/day) | Cell density (cells/ml) Living cells | Cell density (cells/ml) Dead cells | concentration of the antibody (micrograms/ml) |
|---|---|---|---|---|
| 1st day | 0 | $3.1 \times 10^5$ | $0.8 \times 10^4$ | — |
| 3rd day | 0 | $8.7 \times 10^5$ | $2.1 \times 10^4$ | — |
| 4th day | 450 | $1.8 \times 10^6$ | $3.7 \times 10^4$ | — |
| 5th day | 450 | $4.0 \times 10^6$ | $5.2 \times 10^4$ | 46 |
| 6th day | 675 | $7.7 \times 10^6$ | $6.3 \times 10^4$ | 124 |
| 7th day | 675 | $1.3 \times 10^7$ | $1.3 \times 10^5$ | 109 |
| 8th day | 675 | $1.3 \times 10^7$ | $1.5 \times 10^5$ | 127 |

TABLE 9

Fluorinert FC-72 was used as the oxygen supply medium. The average surface area of FC-72 was 10 cm$^2$/ml.

| Time | Feed rate of the fresh medium (ml/day) | Cell density (cells/ml) Living cells | Cell density (cells/ml) Dead cells | concentration of the antibody (micrograms/ml) |
|---|---|---|---|---|
| 1st day | 0 | $2.1 \times 10^5$ | 0 | — |
| 3rd day | 0 | $7.9 \times 10^5$ | $1.1 \times 10^4$ | — |
| 4th day | 450 | $1.7 \times 10^6$ | $2.1 \times 10^4$ | — |
| 5th day | 450 | $3.3 \times 10^6$ | $6.4 \times 10^4$ | 41 |
| 6th day | 675 | $6.7 \times 10^6$ | $1.0 \times 10^5$ | 83 |
| 7th day | 675 | $1.1 \times 10^7$ | $1.3 \times 10^5$ | 98 |
| 8th day | 675 | $1.3 \times 10^7$ | $2.0 \times 10^5$ | 131 |

EXAMPLE 11

Figure 5:
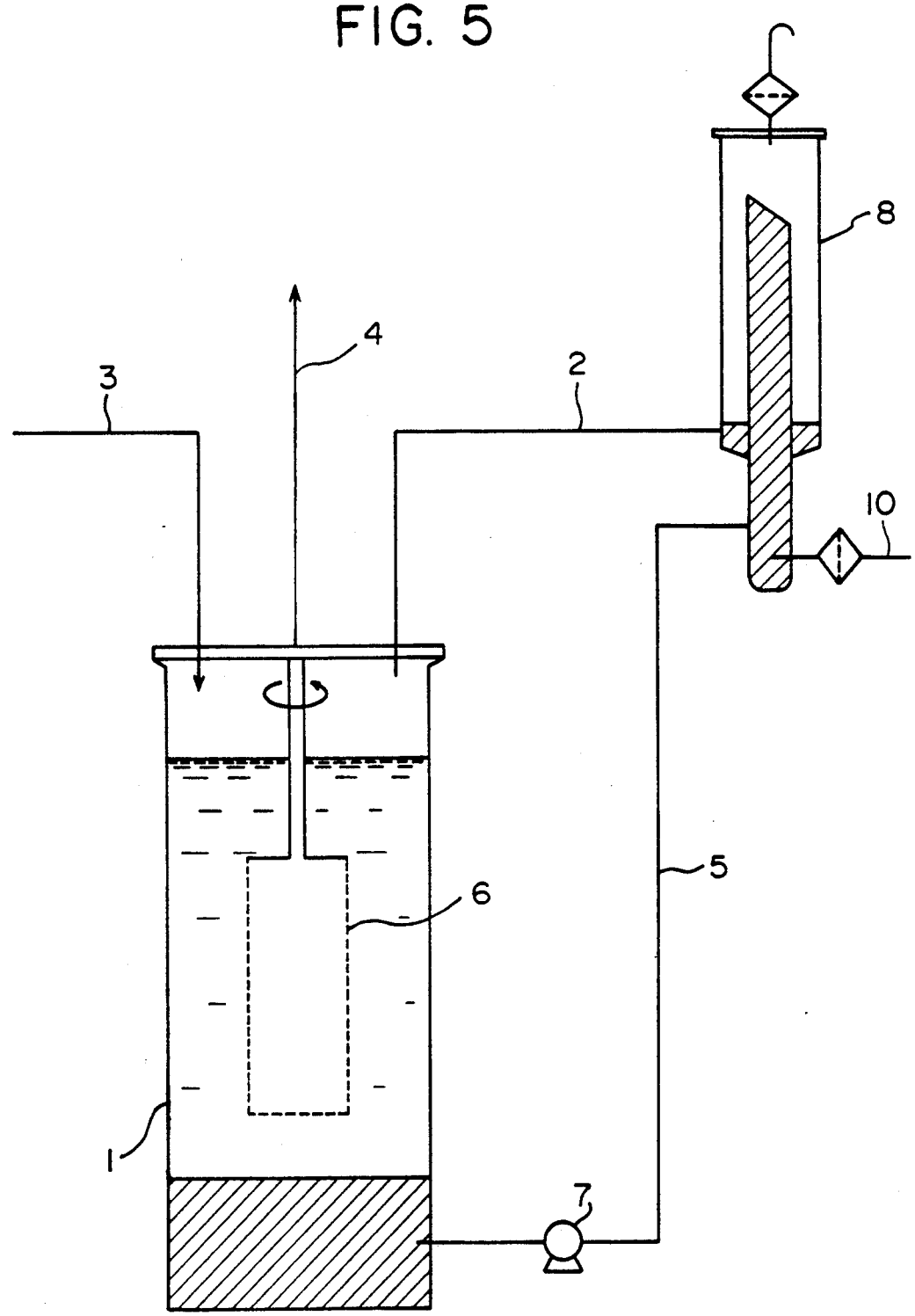
FIG. 5—A tank for large scale cell culture, with line 2 dispersing fluorocarbon droplets above the culture medium.

A cultivation device shown in FIG. 5 was used. In a cultivation tank 1 (25 cm in diameter and 35 cm in height) is provided a cylindrical rotating filter (13 cm in height and 8 cm in outer diameter). This is a sintered metal filter and is impermeable to cells. In the bottom of the cultivation tank 1 is charged in advance 4000 ml of fluorocarbon (Fluorinert FC-40, a product of 3M Company).

The cultivation tank 1 was sterilized in an autoclave, 10 l of RPMI 1640 culture medium containing 10% fetal bovine serum was charged and mouse-mouse hybridoma 4C10B6 (parent cell: P3U1) was seeded in such a manner as to have a cell density of $2.2 \times 10^5$ cells/ml.

Air containing 5% $CO_2$ was passed through the upper part of the cultivation tank and cell culture was performed at 37° C. by rotating the rotating filter at the rotation number of 80 rpm.

On the 3rd day after the cultivation was initiated, cell density reached $7.1 \times 10^5$ cells/ml. From this time on the same culture medium as the above was continuously supplied anew to the cultivation tank at a rate of 10 liters/day through a line 3 of FIG. 5. At the same time the cultivation liquor from which cells were separated by the filter 6 was taken out of the system passing through a line 4. The fresh medium being supplied and the cultivation liquor being taken out were controlled so as to reach the same amounts.

Further, the supply of 5% $CO_2$-containing air was simultaneously stopped, and by operating a pump 7 the fluorocarbon in the cultivation tank was forwarded to a bubble tower 8 through a line 5, and fluorocarbon saturated with oxygen gas was let fall from above as liquid droplets in the cultivation tank passing through a line 2 whereby oxygen was supplied to the cultivation liquor. By controlling the operation of the pump 7 the dissolved oxygen concentration of the cultivation liquor was held at 3 ppm. Liquid droplets of fluorocarbon falling downwardly in the cultivation liquor were about 5 to 6 mm in average diameter, and a ratio of its surface area S to its volume V, S/V, was about 10–12.

From the 6th day on the amount of the medium supplied was set at 20 litres/day.

Cell density and antibody concentration were shown in following Table 10.

TABLE 10

| Cultivation days | Cell density (cells/ml) Live cell | Cell density (cells/ml) Dead cell | Antibody concentration (μg/ml) |
|---|---|---|---|
| 1 | $2.2 \times 10^5$ | 0 | — |
| 2 | $4.0 \times 10^5$ | 0 | 10 |
| 3 | $7.1 \times 10^5$ | 0 | 21 |
| 4 | $1.2 \times 10^6$ | $5.0 \times 10^4$ | 23 |
| 5 | $2.9 \times 10^6$ | $5.1 \times 10^4$ | 39 |
| 6 | $5.3 \times 10^6$ | $7.4 \times 10^4$ | 55 |
| 7 | $8.5 \times 10^5$ | $9.2 \times 10^4$ | 70 |
| 8 | $1.2 \times 10^7$ | $1.1 \times 10^5$ | 90 |
| 9 | $1.3 \times 10^7$ | $1.9 \times 10^5$ | 104 |
| 10 | $1.3 \times 10^7$ | $1.8 \times 10^5$ | 115 |

COMPARATIVE EXAMPLE 2

Figure 6:
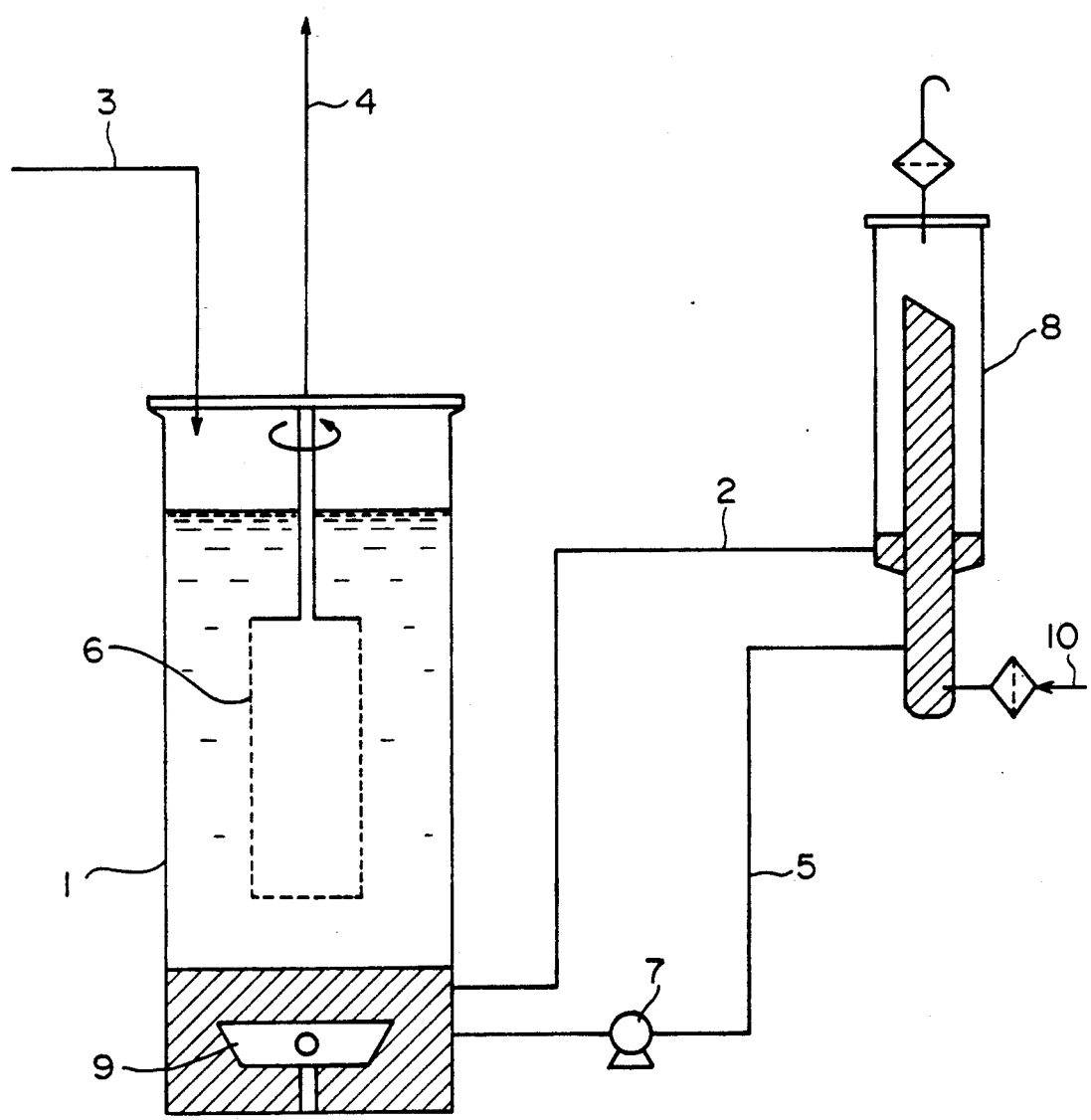
FIG. 6—A tank for large scale cell culture similar to FIG. 5, with the modification that line 2 dispenses fluorocarbon directly to the bottom of the culture and stirring vane 9 is in the fluorocarbon layer.

A cultivation tank shown in FIG. 6 was used. This is the same tank as used in FIG. 5 except that the line 2 is connected to the portion of fluorocarbon in the bottom of the cultivation tank but not to the upper part of the cultivation tank and that a stirring vane 9 to be driven by magnet is provided in the fluorocarbon.

The cultivation tank 1 was sterilized in an autoclave, 10 l of RPMI 1640 culture medium containing 10% fetal bovine serum was charged, and mouse-mouse hybridoma 4C10B6 (parent strain: P3U1) was seeded in such a manner as to have a cell density of $2.1 \times 10^5$ cells/ml, and air containing 5% $CO_2$ was passed through the upper of the cultivation tank and cell culture was performed at 37° C. by rotating the rotating filter 6 at 80 rpm. On the 3rd day after the cultivation was initiated cell density reached $7.0 \times 10^5$ cells/ml. From this time on the same medium as the above was continuously suppled anew to the cultivation tank at a rate of 10 l/day from the line 3 of FIG. 6. At the same time the cultivation liquor from which cells were separated by the filter 6 was taken out of the system through the line 4. The medium being supplied and the cultivation liquor being taken out were controlled so as to reach the same amounts.

Further, the supply of air containing 5% $CO_2$ was simultaneously stopped and by operating the pump 7 the fluorocarbon in the cultivation tank was forwarded to the bubble tower 8 passing through the line 5, and fluorocarbon saturated with oxygen gas was returned to the cultivation tank through the line 2 thereby oxygen was supplied to the cultivation liquor. At that time, the stirring vane 9 in the fluorocarbon was operated whereby the fluorocarbon was stirred and flowed, and the rotation number was set in such a manner that liquid droplets of the fluorocarbon became 2–4 mm in diameter. The rotation number at that time was 350 rpm. By controlling the operation of the pump 7 the dissolved oxygen concentration of the cultivation liquor was held at 3 ppm.

At that time the S/V value of the hydrocarbon, a ration of its surface area S to its volume V, was about 10–20.

On the 5th day when cell density reached $1.9 \times 10^6$ cells/ml, cells were microscopically observed and obviously the cells were found to be mechanically damaged. On the 6th day cell density reached $1.7 \times 10^6$ cells/ml, but cell condition was markedly deteriorated and on the 7th day the cells were all dead.

COMPARATIVE EXAMPLE 3

A cultivation tank shown in FIG. 6 was used. Cell culture was initiated at the same cell density in quite the same manner as in Comparison Example 2. On the 3rd day after the cultivation was initiated cell density reached $7 \times 10^5$ cells/ml. From that time on a fresh medium was continuously supplied to the cultivation tank at a rate of 10 l/day from the line 3. At the same time the cultivation liquor from which cells were separated by the filter 5 was taken out of the system through the line 4. The medium being supplied and the cultivation liquor being taken out were controlled in such a manner as to reach the same amounts.

Further, the supply of air containing 5% $CO_2$ was simultaneously stopped and by operating the pump 7 the fluorocarbon in the cultivation tank was forwarded to the bubble tower 8 through the line 5 and fluorocarbon saturated with oxygen gas was returned to the cultivation tank through the line 2 whereby oxygen was supplied to the cultivation liquor. From that time on the stirring vane 9 in the fluorocarbon was rotated at the rotation number of 80 rpm and the fluorocarbon was flowed. The fluorocarbon was stirred without forming liquid droplets.

By operating the pump 7 the dissolved oxygen concentration of the cultivation liquor was held at 3 ppm.

On the 5th day when cell density reached $2.0 \times 10^6$ cells/ml, the dissolved oxygen concentration of the cultivation liquor could no longer be held at 3 ppm, on the 6th day cell density reached $2.3 \times 10^6$ cells/ml, but the dissolved oxygen concentration became 0 ppm and cell condition was markedly deteriorated and on the 7th day the cells were all dead.

EXAMPLE 12

Figure 7:
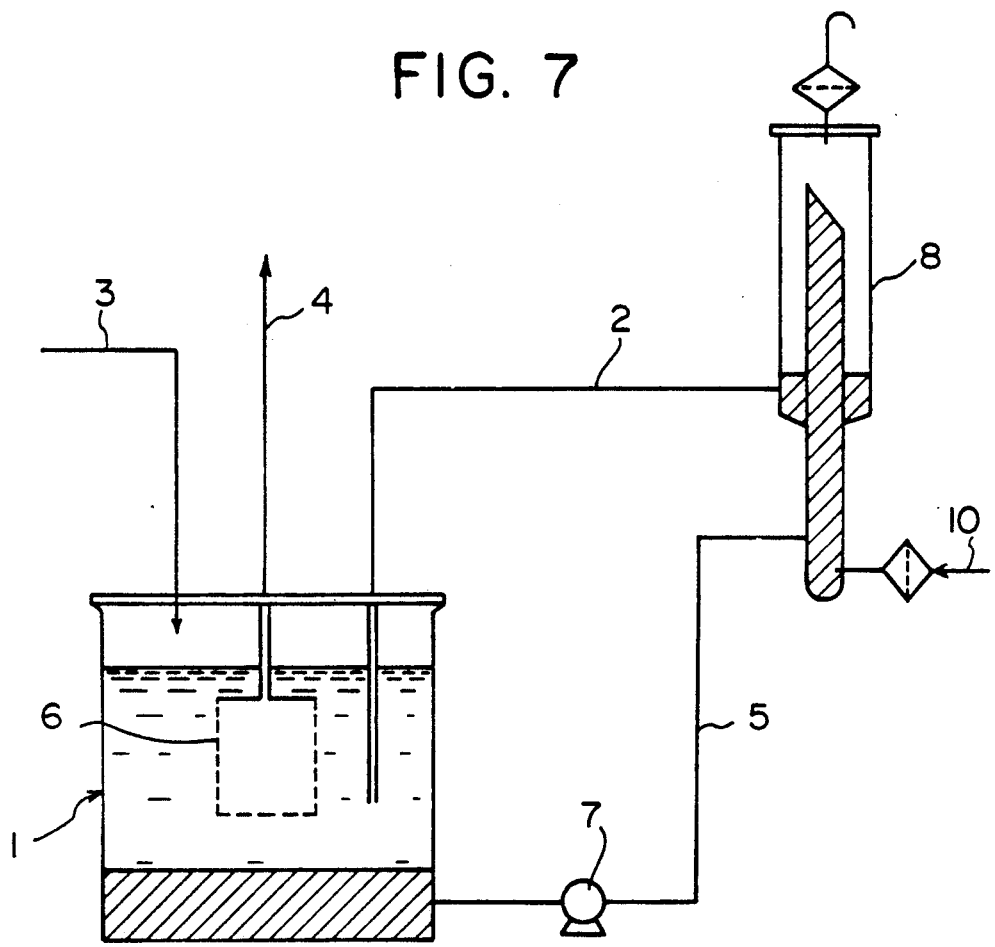
FIG. 7—A tank for large scale cell culture, with line 2 dispersing fluorocarbon directly into the culture medium.

A cultivation device shown in FIG. 7 was used. A cylindrical rotating filter (8 cm in height and 5 cm in outer diameter) is provided in a cultivation tank 1 (15 cm in diameter and 25 cm in height). This is a calcined metal filter and is impermeable to cells. Further, in the bottom of the cultivation tank 1 is charged in advance 1000 ml of Fluorinert FC-40 ( a trademark registered by 3M Company).

The cultivation tank 1 was sterilized in an autoclave, 3 l of RPMI 1640 medium containing 10% fetal bovine serum was charged, and mouse-mouse hybridoma 4C10B6 (parent strain: P3U1) was seeded in such a manner as to have a cell density of $1.9 \times 10^5$ cells/ml. Air containing 5% $CO_2$ was passed through the upper part of the cultivation tank and cell culture was conducted at 37° C. by rotating the rotating filter at the rotation number of 80 rpm. On the 3rd day after the cultivation was initiated cell density reached $6.8 \times 10^5$ cells/ml. From that time on a fresh medium was continuously supplied at a flow rate of 3 l/day from a line 3 of FIG. 7. At the same time the cultivation liquor from which cells were separated by a filter 6 was taken out of the system passing through the line 4. The medium being supplied and the cultivation liquor being taken out were controlled so as to reach the same amounts. Further, on the 4th day when cell density reached $10 \times 10^6$ cells/ml, the dissolved oxygen concentration of the cultivation liquor could no longer be held at 3 ppm. Whereupon, the supply of air containing 5% $CO_2$ was stopped, and by operating a pump 7 the fluorocarbon in the cultivation tank was forwarded to a bubble tower 8 at a flow rate of 500 ml/min. through a line 5. The fluorocarbon was saturated with oxygen in the bubble tower 8, and forwarded to the cultivation tank.

The portion of a line 2 in the cultivation tank is a glass pipe with an inner diameter of 6.3 mm, and its lower end is situated 5.7 cm above the boundary surface between the cultivation liquor and the fluorocarbon. The fluorocarbon falls downwardly in the cultivation liquor as a liquid column with a diameter of 6.3 mm, and no liquid droplets are formed.

S/V, a ration of surface area S to volume V of fluorocarbon, is 6.4. Further, at that time the surface area of the liquid column is 11.3 $cm^2$.

By controlling the operation of the pump the dissolved oxygen concentration of the cultivation liquor was held at 3 ppm.

The amount of the medium supplied from the 6th day on was set at 6 l/day.

Cell density and antibody concentration were shown in Table 11.

TABLE 11

| Cultivation days | Cell density (cells/ml) | | Antibody concentration ($\mu$g/ml) |
| --- | --- | --- | --- |
| | Live cell | Dead cell | |
| 1 | $1.9 \times 10^5$ | 0 | — |
| 2 | $3.9 \times 10^5$ | 0 | — |
| 3 | $6.8 \times 10^5$ | 0 | 4 |
| 4 | $1.0 \times 10^6$ | 0 | 10 |
| 5 | $1.8 \times 10^6$ | $4.1 \times 10^4$ | 13 |
| 6 | $2.6 \times 10^6$ | $5.0 \times 10^4$ | 25 |
| 7 | $3.9 \times 10^6$ | $6.3 \times 10^4$ | 39 |
| 8 | $5.8 \times 10^6$ | $6.9 \times 10^4$ | 59 |
| 9 | $9.1 \times 10^6$ | $7.1 \times 10^4$ | 99 |
| 10 | $1.3 \times 10^7$ | $8.0 \times 10^4$ | 99 |
| 11 | $1.2 \times 10^7$ | $9.3 \times 10^4$ | 105 |

EXAMPLE 13

Figure 8:
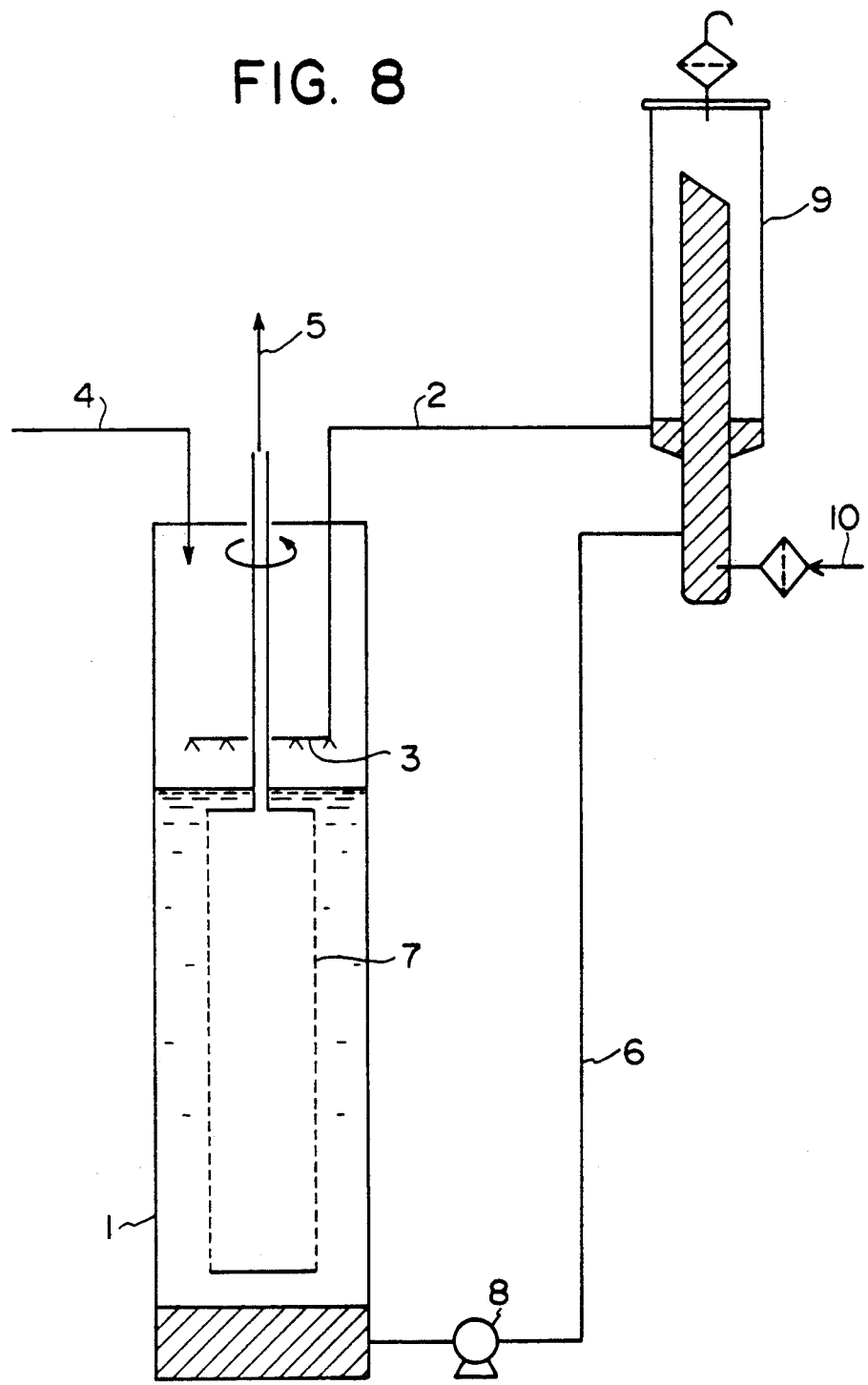
FIG. 8—A tank for large scale cell culture similar to FIG. 5, with the modification that a sparger 3 disperses fluorocarbon above the surface of the culture medium.

A device shown in FIG. 8 of the accompanying drawings was used. A fermentor 1 (having a diameter of 300 mm and a height of 1200 mm) including a cylindrical rotating filter 7 having a height of 650 mm and an outside diameter of 150 mm (impermeable to cells but permeable to liquid components; made of sintered stainless steel) was sterilized. Into the fermentor was fed 15 liter of Perfluorocarbon FC-40 sterilized beforehand. Successively, 40 liter of PRMI 1640 medium sterilized by filtration containing 10% fatal bovine serum was fed into the fermentor. By operating the pump 8 the fluorocarbon gathered at the base of the fermentor was fed into a bubble tower 9. The bubble tower 9 is equipped with an oxygen blower line 10. The fluorocarbon overflown from the tower 9 was circulated to the cultivation system in the form of a droplet from the sparger 3 mounted in the fermentor via line 2. In this sparger 3 are made 50 nozzles each having a diameter of 0.5 mm. The pump 8 was stopped after confirming that the above operation was made stably. Rotation of the filter 7 was started at 90 r.p.m. Then mouse-mouse hybridoma 4C10B6 cells were cells/ml. The pump 8 is connected to a dissolved oxygen system disposed in the fermentor. This enables one to control the dissolved oxygen system in the fermentor automatically. After seeding the cells, a preset value of the dissolved oxygen system was fixed at 3 ppm. The cultivation temperature was maintained at 37° C. by circulating a hot water through the jacket of the fermentor. In this state a batch cultivation was conducted for 5 days.

On the 6th day counted from the start of the cultivation the viable cell density was measured and proved to be $5.8 \times 10^6$ cells/ml. Thus, withdrawal of a culture supernatant from the line 5 was started. Its velocity was fixed at 20 liter/day. The viable cell density on the 7th day was $1.1 \times 10^6$ cells/ml and the concentration of the antibody in the culture supernatant, 52 μ/ml. The velocity of withdrawing the culture supernatant was changed into 40 liter/day on the 8th day and 80 liter/day on the 9th day. The results of the cultivation were shown in Table 12.

TABLE 12

FC-40 was used as the oxygen supply medium. The average surface area of FC-40 was 73 cm²/ml.

| Time | Feed rate of the fresh medium (ml/day) | Cell density (cells/ml) | | concentration of the antibody (micrograms/ml) |
| --- | --- | --- | --- | --- |
| | | Living cells | Dead cells | |
| 1st day | 0 | $2.1 \times 10^4$ | 0 | — |
| 3rd day | 0 | $7.9 \times 10^4$ | 0 | — |
| 5th day | 0 | $3.0 \times 10^5$ | 0 | — |
| 6th day | 20 | $5.8 \times 10^5$ | $1.1 \times 10^4$ | — |
| 7th day | 20 | $1.1 \times 10^6$ | $2.1 \times 10^4$ | 52 |
| 8th day | 40 | $2.0 \times 10^6$ | $2.4 \times 10^4$ | 123 |
| 9th day | 80 | $3.8 \times 10^6$ | $7.1 \times 10^4$ | 132 |
| 10th day | 80 | $7.4 \times 10^6$ | $1.8 \times 10^5$ | 104 |
| 11th day | 80 | $8.3 \times 10^6$ | $3.8 \times 10^5$ | 101 |

EXAMPLE 14

Figure 9:
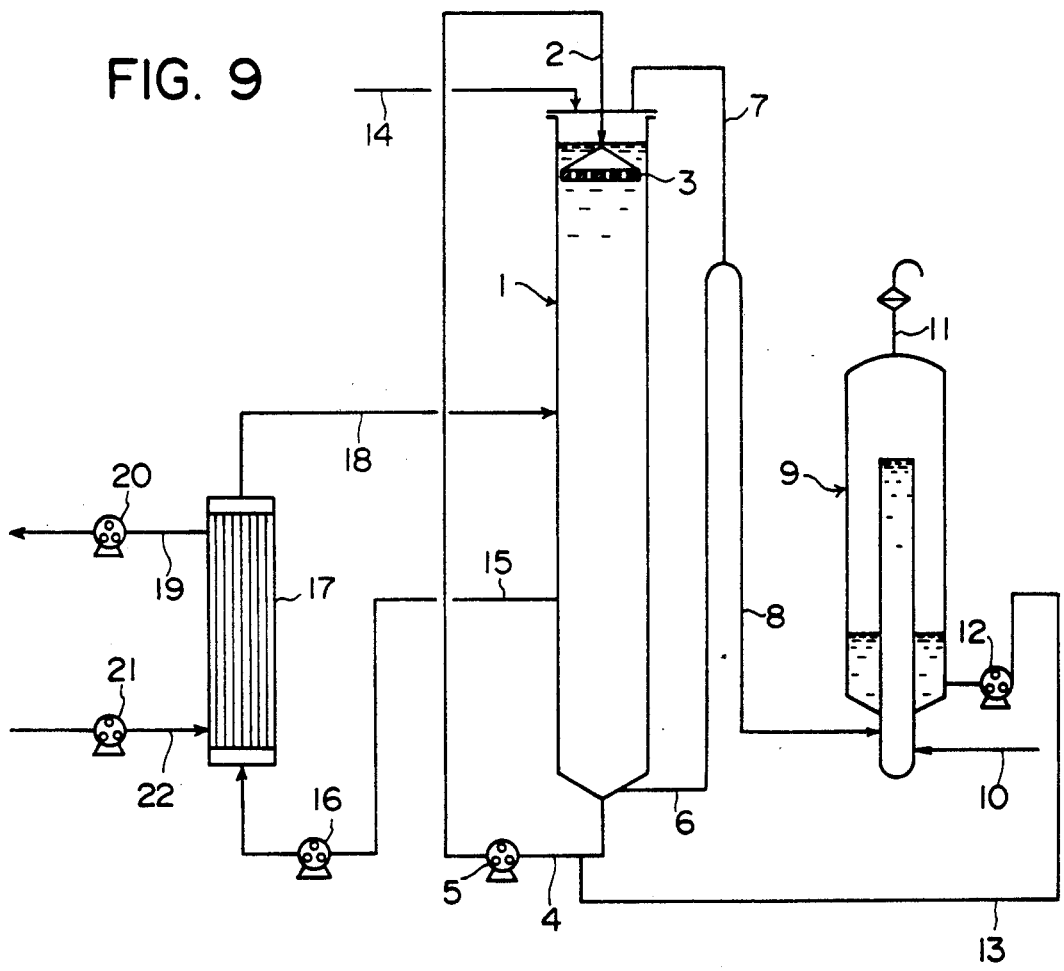
FIG. 9—A glass device for cell culture in which the cells are grown in a hollow fiber filter module 17.

A device shown in FIG. 9 was used. A fermentor 1 was made of glass and had an inside diameter of 15 mm and a height of 1,000 mm. It included a sparger 3 (made of SUS 316 stainless steel) for dispersion of a fluorocarbon which had four nozzles with a diameter of 1 mm.

First, 120 ml of the same culture medium as used in Example 1, sterilized by filtration, was charged into the fermentor. Separately, 50 ml of a fluorocarbon (Fluorinert FC-77; trade names for fluorocarbons produced by 3M Company) which had been deoxygenated with nitrogen gas and sterilized by filtration was introduced into the fermentor. The fluorocarbon was introduced into line 4, pump 5, line 6, line 8, bubble tower 9, pump 12 and line 13. By operating the pump 5, the fluorocarbon was fed into the cultivation system from the sparger 3. The fluorocarbon which left the sparger was in the form of liquid droplets and had an average surface area of 42 cm²/ml. Pure oxygen gas was blown into the bubble tower 9 through line 10. The fluorocarbon which absorbed oxygen was fed into the fermentor automatically through pump 12, line 13, line 4, pump 5 and line 2 so that the concentration of dissolved oxygen in the fermentor became 3 ppm. The fluorocarbon which gathered at the bottom of the fermentor was sent to the bubble tower 9 through lines 6 and 8. Since a communication pipe 7 is attached to the fermentor and the lines 6 and 8, the liquid level of the fluorocarbon in the fermentor was maintained constant.

When the above condition became stable, mousehuman hybridoma H-2 (a human IgG-producing hybridoma obtained by fusing mouse myeloma cells P3-X63-Ag8-U1 with human B cells) was seeded at a cell density of $1.5 \times 10^5$ cells/ml, and the batch cultivation was started at 37° C. On the 3rd day the viable cell density reached $5.3 \times 10^5$ cells/ml. Thus, the reflux was started. Namely, in FIG. 9 by operating the pump 16 a culture mixture was fed into a hollow fiber filter module 17 from the fermentor 1 via line 15. Part of the cultivation liquor in the culture mixture was withdrawn from line 19 to the outside of the system through the hollow fiber of the module 17 via the pump 20. The culture mixture mixing the cells in a condensed state therein was refluxed to the fermentor via line 18. The pump 20 was stopped for one hour once a day and by operating the pump 21 a fresh medium was fed via line 22 thereby to conduct a flow washing of the hollow fiber filter. Further, a fresh medium was supplied into the fermentor via line 14 to insure that the liquid level of the fermentor be constant. The results of cultivation obtained by the above operation were shown in Table 13.

TABLE 13

| Time | Feed rate of the fresh medium (ml/day) | Cell density (cells/ml) | | concentration of the antibody (micrograms/ml) |
| --- | --- | --- | --- | --- |
| | | Living cells | Dead cells | |
| 1st day | 0 | $1.5 \times 10^5$ | 0 | — |
| 3rd day | 50 | $5.3 \times 10^5$ | $1.3 \times 10^4$ | — |
| 4th day | 100 | $1.0 \times 10^6$ | $2.6 \times 10^4$ | 24 |
| 5th day | 200 | $1.8 \times 10^6$ | $3.2 \times 10^4$ | 18 |
| 6th day | 350 | $3.9 \times 10^6$ | $4.8 \times 10^4$ | 24 |
| 7th day | 350 | $7.2 \times 10^6$ | $2.3 \times 10^5$ | 27 |
| 8th day | 350 | $1.2 \times 10^7$ | $4.2 \times 10^5$ | 44 |
| 9th day | 350 | $1.1 \times 10^7$ | $6.2 \times 10^5$ | 53 |

What is claimed is:

1. A method of cultivating animal or plant cells, which consists essentially of contacting a cultivation liquor having animal or plant cells suspended therein with a liquid fluorocarbon having molecular oxygen dissolved therein, characterized in that said cultivation liquor forms a continuous suspension phase which has cell densities of at least $4 \times 10^6$ cells/ml, that said contact is made by feeding said liquid fluorocarbon into the cultivation liquor from above the cultivation liquor such that 1 ml of liquid fluorocarbon has a surface area of about 6 to about 300 cm² whereby the liquid fluorocarbon falls downward through the cultivation liquor by gravity, and that said cultivation liquor has a volume of at least about 10 liters.

2. The method of claim 1 wherein the liquid fluorocarbon is in the form of a liquid droplet.

3. The method of claim 1 wherein 1 ml of the liquid fluorocarbon has a surface area of about 10 to about 200 cm².

4. The method of claim 1 wherein the cultivation liquor has a volume of at least about 30 liters.

5. The method of claim 1 wherein the density of the animal cells in the cultivation liquor is at least $6 \times 10^6$ cells/ml.

6. The method of claim 1 wherein the cultivation liquor is separated and withdrawn from the cultivation system consisting substantially of the cultivation liquor, the animal or plant cells and the liquid fluorocarbon continuously or stepwise, and in the meantime, a fresh liquid medium in an amount corresponding to the withdrawn cultivation liquor is fed into the cultivation system continuously or stepwise.

7. The method of claim 1 wherein no external positive stirring operation is exerted on the cultivation system consisting substantially of the cultivation liquor and the liquid fluorocarbon.

8. The method of claim 1 wherein the liquid fluorocarbon is substantially nontoxic to the animal or plant cells.

9. The method of claim 1 wherein the liquid fluorocarbon is a perfluorocarbon.

10. The method of claim 1 wherein the liquid fluorocarbon is selected from the group consisting of perfluoroalkanes having 6 to 20 carbon atoms, perfluorocycloalkanes having 5 to 14 carbon atoms which may be substituted by perfluoroalkyl groups having 1 to 5 carbon atoms, perfluorofurans substituted by perfluoroalkylyl groups having 1 to 7 carbon atoms, perfluorotetrahydrofurans substituted by perfluoroalkyl groups having 1 to 7 carbon atoms, perfluoropyrans substituted by perfluoroalkyl groups having 1 to 6 carbon atoms, perfluorotetrahydropyrans substituted by perfluoroalkylyl groups having 1 to 6 carbon atoms, perfluoroadamantanes which may be substituted by perfluoroalkyl groups having 1 to 5 carbon atoms, and tertiary amino group substituted products of said fluorocarbons.

11. The method of claim 1 wherein the animal cells are anchorage-independent cells, and are suspended in the cultivation liquor without being supported on a carrier.

12. The method of claim 1 wherein the animal cells are anchorage-independent, and are suspended in the cultivation liquor while being immobilized with a gel.

13. The method of claim 1 wherein the animal cells are anchorage-dependent cells, and are suspended in the cultivation liquor while being supported on a carrier.

14. The method of claim 1 wherein the cells in an animal cells.

15. The method of claim 1 wherein the cultivation liquor having the animal cells suspended therein is a serum-free culture medium.

16. A method for cultivating animal or plant cells, which comprises
   (1) feeding a liquid fluorocarbon having molecular oxygen dissolved therein from above into a cultivation tank containing a continuous phase of a cultivation liquor having animal or plant cells suspended therein in a density of at least $4 \times 10^6$ cells/ml to thereby contact them with each other while 1 ml of the liquid fluorocarbon has a surface area of about 6 to about 300 $cm^2$; said cultivation liquor having a volume of at least about 10 liters
   (2) withdrawing a heavy phase composed substantially of the fluorocarbon from the bottom of the cultivation tank;
   (3) dissolving molecular oxygen in the fluorocarbon in the heavy phase; and
   (4) thereafter using the liquid fluorocarbon having molecular oxygen dissolved therein in step (1).

17. The method of claim 16 wherein the cultivation liquor is separated and withdrawn from the cultivation system consisting substantially of the cultivation liquor, the animal or plant cells and the liquid fluorocarbon continuously or stepwise, and in the meantime, a fresh liquid medium in an amount corresponding to the withdrawn cultivation liquor is fed into the cultivation system continuously or stepwise.

* * * * *